(12) United States Patent
Piron et al.

(10) Patent No.: US 10,026,174 B2
(45) Date of Patent: Jul. 17, 2018

(54) METHOD, SYSTEM AND APPARATUS FOR AUTOMATICALLY EVALUATING RESECTION ACCURACY

(71) Applicants: Cameron Anthony Piron, Toronto (CA); Alex Panther, Toronto (CA)

(72) Inventors: Cameron Anthony Piron, Toronto (CA); Alex Panther, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/535,227

(22) PCT Filed: Jan. 7, 2015

(86) PCT No.: PCT/CA2015/000013
§ 371 (c)(1),
(2) Date: Jun. 12, 2017

(87) PCT Pub. No.: WO2016/109878
PCT Pub. Date: Jul. 14, 2016

(65) Prior Publication Data
US 2017/0358083 A1    Dec. 14, 2017

(51) Int. Cl.
*G06K 9/00* (2006.01)
*G06T 7/00* (2017.01)
(Continued)

(52) U.S. Cl.
CPC ............ *G06T 7/0016* (2013.01); *A61B 34/20* (2016.02); *A61B 34/30* (2016.02); *A61B 90/361* (2016.02);
(Continued)

(58) Field of Classification Search
CPC ......... G06T 7/0016; G06T 2207/10088; G06T 2207/30016; G06T 2207/30096;
(Continued)

(56) References Cited

U.S. PATENT DOCUMENTS

| 7,876,939 B2 * | 1/2011 | Yankelevitz | A61B 5/1075 382/128 |
| 7,968,851 B2 * | 6/2011 | Rousso | G01T 1/161 250/370.09 |

(Continued)

OTHER PUBLICATIONS

International Preliminary Report on Patentability dated May 5, 2017 for PCT International Patent Application No. PCT/CA2015/000013.
(Continued)

*Primary Examiner* — Ali Bayat
(74) *Attorney, Agent, or Firm* — Perry + Currier (57) ABSTRACT

A method of automatically evaluating resection accuracy, is provided. The method includes preoperatively obtaining a first image of a volume of patient tissue using an imaging modality configured according to a scanning parameter, and storing the scanning parameter. An identifier of a target region corresponding to a target portion of the volume is received and stored in association with the first image. A second image is obtained of a resected tissue sample from the volume, using the imaging modality configured according to the scanning parameter. Based on a comparison of the first image and the second image, a determination is made whether the entire target region is represented in the second image. The method includes controlling an output device to present an indication, based on the determination, of whether the tissue sample contains the entire target portion.

13 Claims, 8 Drawing Sheets

(51) Int. Cl.
*G06F 19/00* (2018.01)
*A61B 90/00* (2016.01)
*A61B 34/30* (2016.01)
*A61B 34/20* (2016.01)

(52) U.S. Cl.
CPC ........ *G06F 19/321* (2013.01); *G06F 19/3481* (2013.01); *A61B 2034/2051* (2016.02); *A61B 2034/2055* (2016.02); *A61B 2090/365* (2016.02); *A61B 2090/374* (2016.02); *A61B 2090/3979* (2016.02); *A61B 2576/026* (2013.01); *G06T 2207/10088* (2013.01); *G06T 2207/30016* (2013.01); *G06T 2207/30096* (2013.01)

(58) Field of Classification Search
CPC ....... A61B 34/20; A61B 34/30; A61B 90/361; A61B 2090/365; A61B 2090/374; A61B 2090/3979; A61B 2090/3954; G06F 19/321; G06F 19/3481
See application file for complete search history.

(56) References Cited

U.S. PATENT DOCUMENTS

| | | | | |
|---|---|---|---|---|
| 8,731,255 | B2* | 5/2014 | El-Baz | G06T 7/0016 382/128 |
| 9,070,181 | B2* | 6/2015 | Wu | G06T 7/0012 |
| 9,521,961 | B2* | 12/2016 | Silverstein | A61B 5/042 |
| 2012/0063644 | A1 | 3/2012 | Popovic | |
| 2012/0184844 | A1 | 7/2012 | Gielen et al. | |
| 2012/0283574 | A1 | 11/2012 | Park et al. | |
| 2014/0363063 | A1 | 12/2014 | Hendriks et al. | |
| 2016/0292859 | A1* | 10/2016 | Magda | G06T 7/33 |

OTHER PUBLICATIONS

International Search Report dated Oct. 8, 2015 for International Patent Application No. PCT/CA2015/000013.

Written Opinion dated Oct. 8, 2015 for International Patent Application No. PCT/CA2015/000013.

* cited by examiner

METHOD, SYSTEM AND APPARATUS FOR AUTOMATICALLY EVALUATING RESECTION ACCURACY

FIELD

The specification relates generally to medical imaging, and specifically to a method, system and apparatus for automatically evaluating resection accuracy.

BACKGROUND

Some surgical planning and navigation systems allow for preoperative identification of target areas within patient tissues. Some systems also allow for the preoperative identification of trajectories for surgical instruments to reach the above-mentioned target areas. However, particularly in the case of tissue resection procedures, current planning and navigation systems are unable to provide medical staff with confirmation that the planned target areas have been fully resected. Instead, such confirmation is generally provided via manual sampling of resected tissue, for example by a pathologist. Such sampling may not be completed in time to correct the surgical procedure if some target tissue has not been resected, and in addition the sampling may be prone to errors.

SUMMARY

According to an aspect of the specification, a computing device is provided for automatically evaluating resection accuracy, comprising: a memory; an output device; and a processor interconnected with the memory and the output device, the processor configured to: preoperatively obtain a first image of a volume of patient tissue using an imaging modality configured according to a scanning parameter; store the scanning parameter in the memory; receive and store, in association with the first image, an identifier of a target region corresponding to a target portion of the volume; responsive to resection of a tissue sample from the volume, obtain a second image of the tissue sample using the imaging modality configured according to the scanning parameter; determine, based on a comparison of the first image and the second image, whether the entire target region is represented in the second image; and control the output device to present an indication, based on the determination, of whether the tissue sample contains the entire target portion.

According to another aspect of the specification, a method of automatically evaluating resection accuracy is provided, comprising: preoperatively obtaining a first image of a volume of patient tissue using an imaging modality configured according to a scanning parameter; storing the scanning parameter in a memory; receiving and storing, in association with the first image, an identifier of a target region corresponding to a target portion of the volume; responsive to resection of a tissue sample from the volume, obtaining a second image of the tissue sample using the imaging modality configured according to the scanning parameter; determining, based on a comparison of the first image and the second image, whether the entire target region is represented in the second image; and controlling an output device to present an indication, based on the determination, of whether the tissue sample contains the entire target portion.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
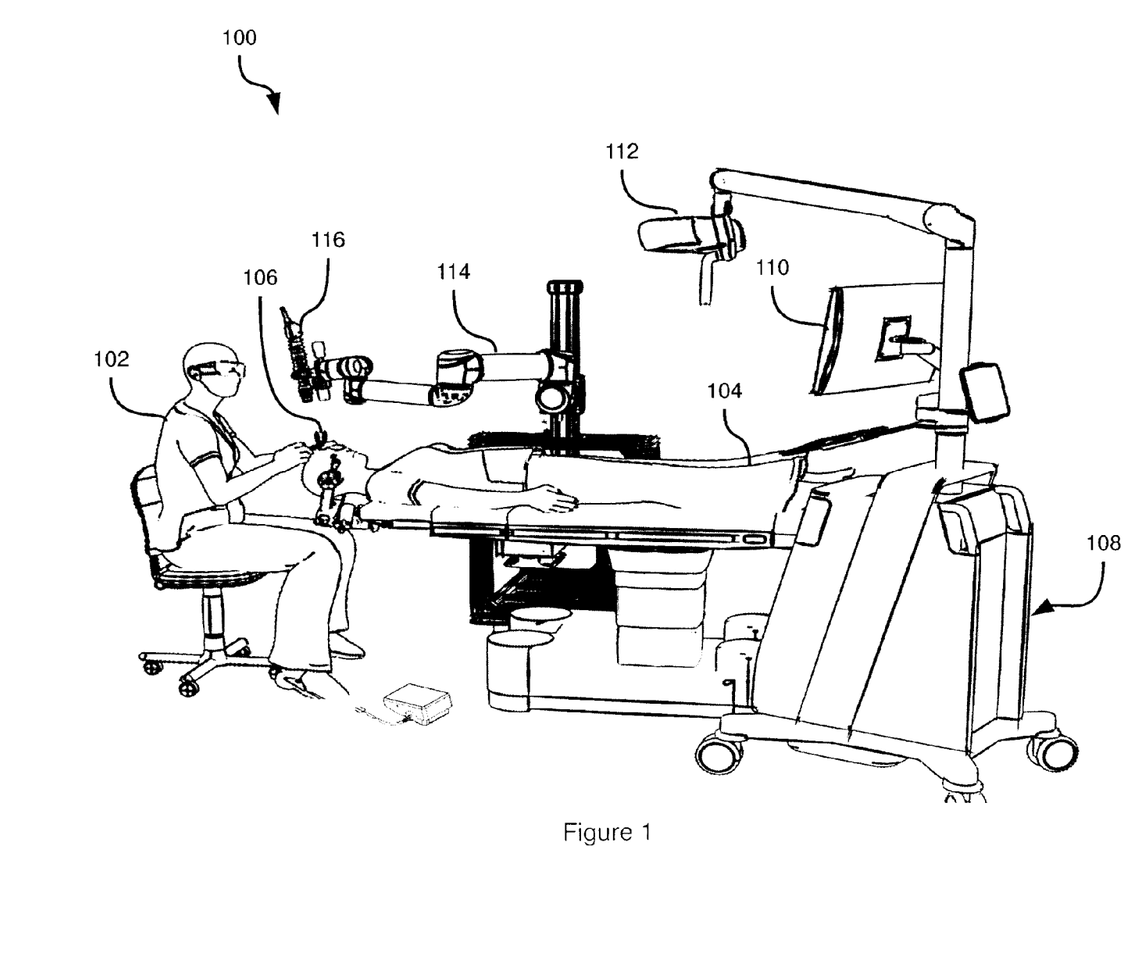
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 106, any of the above-mentioned surgical tools, or any combination thereof. Such markers, also referred to as fiducial markers, may also be mounted on patient 104, for example at various points on patient 104's head. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 106 by robotic arm 114, and may capture images of the brain of patient 104 for presentation on display 110. The movement of robotic arm 114 to place external scope 116 correctly over access port 106 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of patient 104's brain or portions thereof. Such preoperative images may be collected using any of a variety of imaging modalities, such as Magnetic Resonance Imaging (MRI), Optical Coherence Tomography (OCT), ultrasound, Computed Tomography (CT), optical spectroscopy and the like. For each of the above-mentioned imaging modalities, various imaging techniques may be used. Polarization Sensitive OCT and OCT elastography are exemplary uses of the OCT modality. Diffusion MRI (also referred to as diffusion tensor imaging, DTI) is an example use of the MRI modality. Raman spectroscopy is an example use of optical spectroscopy. A variety of other examples of the above modalities will also occur to those skilled in the art.

Preoperative images may be used for planning purposes. Examples of planning activities include marking, in the preoperative images, the location of a target portion of patient tissue. Such a target portion may include a tumor to be resected, for example. During the procedure, additional images (referred to as intraoperative images) may be collected from the brain of patient 104, using any suitable ones of the above-mentioned modalities (it will be apparent to those skilled in the art that some imaging modalities are less suitable or unsuitable for preoperative use, while other imaging modalities are less suitable or unsuitable for intraoperative use). In addition, as will be discussed below in greater detail, further images may be acquired during the procedure (or after the procedure has concluded) of tissue samples resected from patient 104.

As will be described in further detail below, the computing device housed in equipment tower 108 can perform various actions to employ the above-mentioned preoperative images and intraoperative images to automatically evaluate the accuracy of a resection procedure, in comparison with the planned resection.

Figure 2:
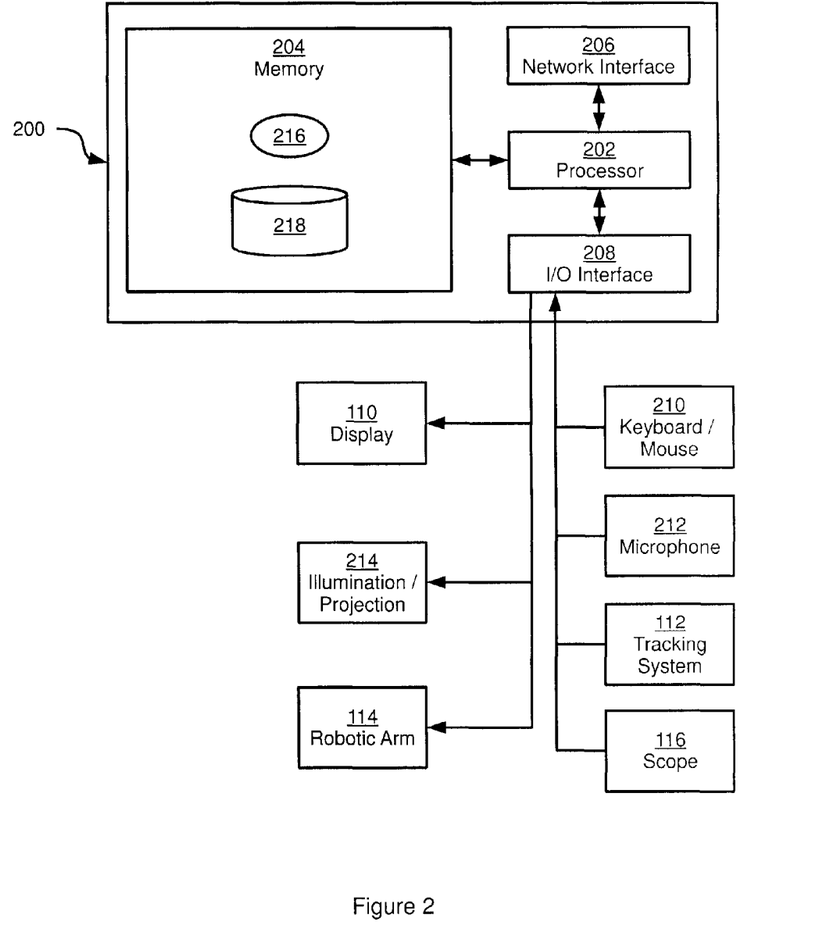
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, a resection evaluation application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository can contain surgical planning data, preoperative and intraoperative images, and the like, as will be seen below.

As mentioned above, computing device 200 is configured, via the execution of application 216 by processor 202, to perform various functions to evaluate the accuracy of a resection procedure in order to confirm whether the planned target portion of patient 104's brain (or other tissue volume) was actually resected during the procedure. Those functions will be described in further detail below.

Figure 3:
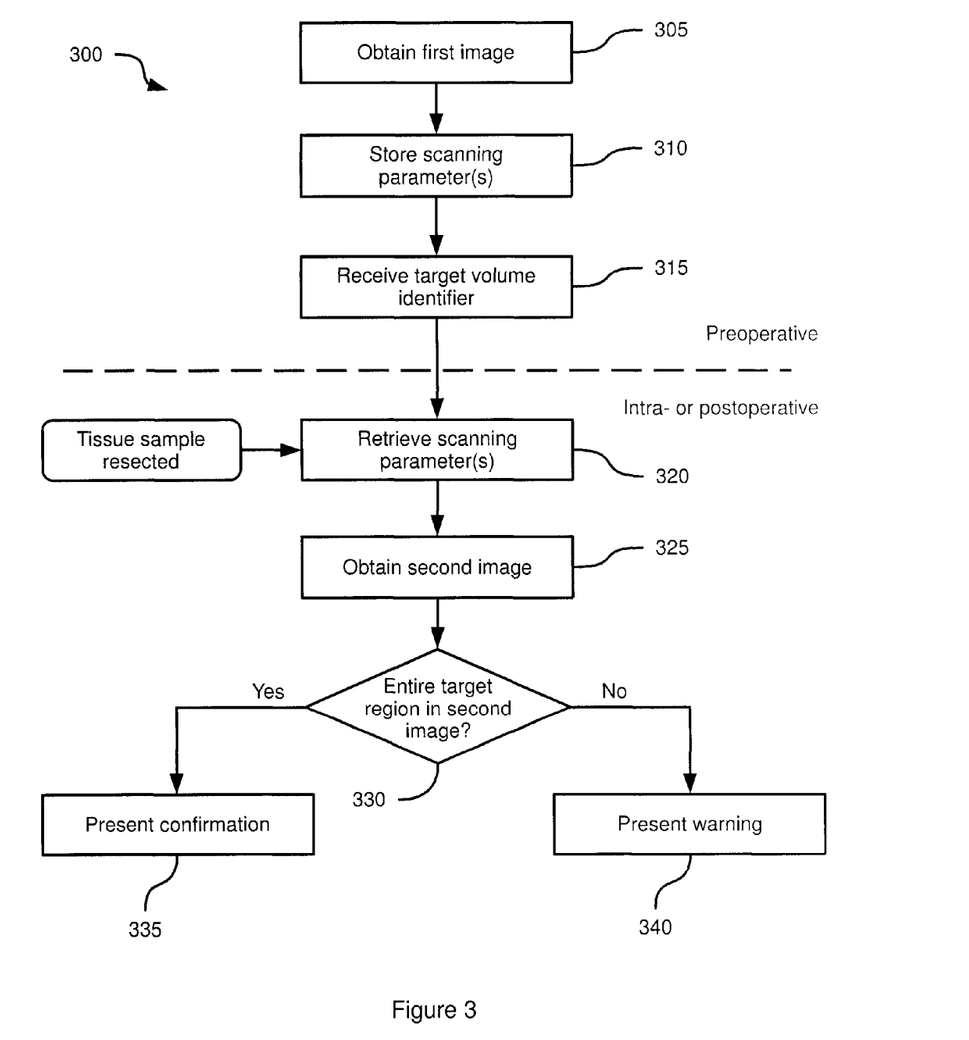
FIG. 3 depicts a method of evaluating resection accuracy, according to a non-limiting embodiment.

Turning now to FIG. 3, a method 300 of automatically evaluating resection accuracy will be discussed in conjunction with its performance on computing device 200. Computing device 200, via the execution of application 216 (and the accompanying processing of data in repository 218), is configured to perform the blocks of method 300. Method 300 may, however, also be performed in other systems and by other computing devices.

Beginning at block 305, computing device 200 is configured to obtain a first image of a volume of tissue of patient 104. In the present example, the volume of tissue is the brain, or at least a portion thereof. In other embodiments, however, computing device 200 can perform method 300 in connection with surgical procedures to be performed on other organs. Thus, the image obtained at block 305 may alternatively be an image of all or part of a liver, breast, prostate, or the like. More generally, the image obtained at block 305 is an image of any tissue volume that is suitable for "en bloc" resection of a target portion of tissue.

The image obtained at block 305 is a preoperative image of the volume of patient tissue. The first image can be obtained using any imaging modality suitable for preoperative imaging. In the present example, the first image is obtained using MRI as an imaging modality. Thus, to obtain the first image, processor 202 can be configured to send instructions (via I/O interface 208 or network interface 206) to a first imaging device, such as an MRI scanner (not shown). The instructions cause the first imaging device to capture the first image and return the first image to computing device 200. In other embodiments, a different computing device may be coupled to the first imaging device and control the first imaging device to capture the first image. In such embodiments, computing device 200 does not exert direct control over the first imaging device, and thus obtaining the first image at block 305 can be achieved at computing device 200 by requesting the first image from such other computing device, or by retrieving the first image from memory 204.

Figure 4:
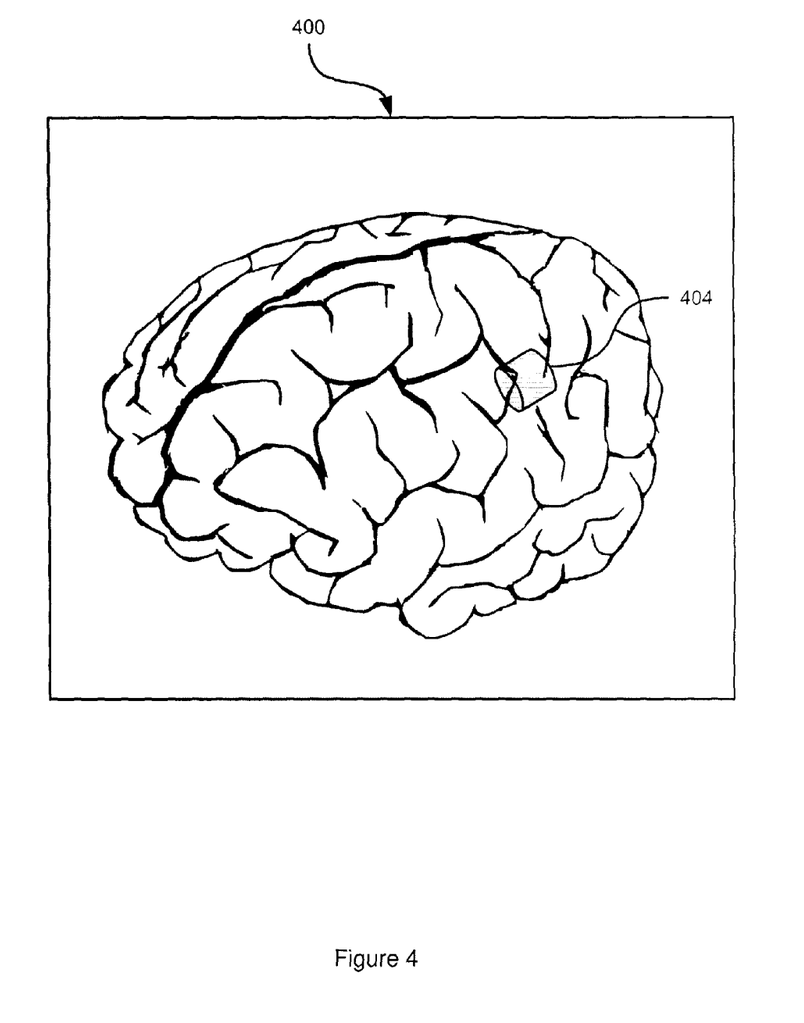
FIG. 4 depicts a first image obtained in the method of FIG. 3, according to a non-limiting embodiment.

Referring to FIG. 4, an example first image 400 is depicted. First image 400, in the present embodiment, is an MRI scan (simplified for illustration in FIG. 4). As seen in FIG. 4, image 400 depicts a tumor 404 within the brain of patient 104. Tumor 404 may be the target of a resection procedure, as will be discussed below.

Returning to FIG. 3, having obtained the preoperative image at block 305, computing device 200 is configured at block 310 to store at least one scanning parameter used to acquire the first image. As will now be apparent to those skilled in the art, the first image, and indeed any preoperative or intraoperative images, is acquire using an imaging modality configured according to a variety of scanning parameters. In the present example, in which the modality used to acquire the first image is MRI, scanning parameters define the MRI protocol used by the first imaging device to acquire the first image. The scanning parameters can therefore include a magnetic field strength, one or more pulse sequences, and the like. The scanning parameters can also be referred to collectively by a protocol identifier (e.g. the T1-weighted MRI protocol refers to a predetermined set of scanning parameters). At block 310, computing device 200 stores the scanning parameters in conjunction with image 400 in memory 204 (for example, in repository 218).

At block 315, computing device 200 is configured to receive and store, in association with first image 400, an identifier of a target region in image 400. The target region corresponds to a target portion of the volume of patient tissue depicted by image 400. Receiving the target region identifier can be achieved in a variety of ways. For example, processor 202 can control display 110 to present image 400, and subsequently receive a selection of the target region within image 400, for example via keyboard/mouse 210. In other embodiments, the target region can be automatically identified by processor 202 by detecting boundaries or edges within image 400. For example, tumor tissue generally has a different appearance in MRI images than healthy tissue, as seen in FIG. 4. Processor 202 can be configured to detect areas in image 400 that have different characteristics (brightness, contrast, and the like) from surrounding areas.

The format in which the target region identifier is stored is not particularly limited. For example, a set of coordinates identifying the target region within image 400 can be stored in memory 204. In other examples, the target region can be identified directly within image 400 as metadata (e.g. a field in image 400 containing the above-mentioned set of coordinates, or a flag set on each of the voxels in image 400 contained within the target region).

In the present example performance of method 300, it is assumed that the target region coincides with tumor 404 as shown in image 400. In other examples, however, the target region can encompass an area greater or smaller than tumor 404. In still other examples, the target region can be entirely independent from tumor 404 (indeed, method 300 can be performed in connection with patients without tumors). In general, the target region corresponds to the target portion of patient 104 that is to be resected.

Following the performance of block 315, computing device 200 is configured to perform block 320, after the surgical procedure has begun. That is, as indicated in FIG. 3, the blocks of method 300 after block 315 are performed intraoperatively or postoperatively.

More specifically, in response to resection of a tissue sample from the volume of patient tissue depicted in image 400, at block 320 computing device 200 is configured to retrieve the scanning parameters stored at block 310. Thus, processor 202 retrieves the scanning parameters from memory 204. In some embodiments, processor 202 can be configured to retrieve additional scanning parameters instead of, or in addition to, those stored at block 310. For example, memory 204 may store a look-up table or other data structure that contains scanning parameters for controlling the first imaging device, and corresponding scanning parameters for controlling a second imaging device. The second imaging device can be, for example, a further MRI scanner (including an MRI scanner having a smaller, less powerful magnet that may be more suitable for use intraoperatively, in an operating theatre). The corresponding scanning parameters contained in the look-up table can be selected to control their respective imaging devices to generate closely matching images (in terms of contrast and other image properties).

Having retrieved the scanning parameters at block 320, at block 325 computing device 200 is configured to obtain a second image of the resected tissue sample using the same imaging modality as was used to obtain the first image, configured according to the scanning parameters retrieved at block 320 (in other words, the same scanning parameters as those used to acquire the first image).

Although the same imaging modality (MRI, in the present example) is used to obtain the second image, it is not necessary to use the same imaging device as was employed to obtain the first image. The acquisition of the first image was preoperative, and thus required that patient 104, or at least a sizeable portion of patient 104 (e.g. the entire head of patient 104) be placed within the first imaging device. In the case of MRI, the first image may therefore be acquired using a large-scale MRI scanner. Such MRI scanners are typically installed in separate facilities from operating theatre 100. The second image, however, is generally of a relatively small (compared to the size of patient 104, or even to the size of patient 104's head) sample of tissue. The second image can therefore be acquired using a smaller MRI scanner, such as an MRI scanner installed within operating theatre 100. In some embodiments, however, both the first and second images may be acquired using the same imaging devices.

Figure 5:
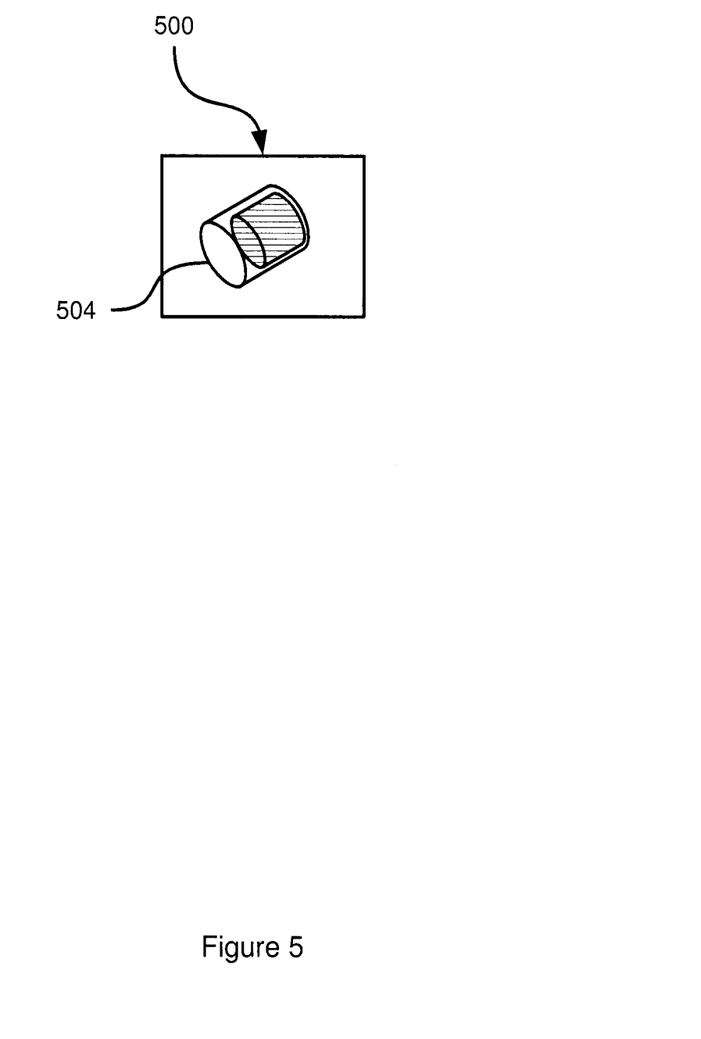
FIG. 5 depicts a second image obtained in the method of FIG. 3, according to a non-limiting embodiment.

The second image obtained at block 325 can be obtained by, for example, transmitting instructions from processor 202 to an imaging device (whether the first imaging device mentioned earlier or the second imaging device). The instructions can include the scanning parameters retrieved at block 320. Turning to FIG. 5, an example second image 500 is depicted of a tissue sample 504 resected from the brain of patient 104. Image 500 is stored in memory 204, for example in repository 218.

Returning to FIG. 3, following the acquisition of second image 500, computing device 200 is configured at block 330 to determine, based on a comparison of first image 400 and second image 500, whether the entire target region identified at block 315 is represented in second image 500.

The determination at block 330 can include registering first image 400 and second image 500 (that is, placing both images in a common frame of reference). The registration can be performed according to any suitable image registration technique. For example, feature-based registration, intensity-based registration, or a combination thereof can be applied. In some embodiments, quantitative registrations parameters may also be employed, as discussed in Applicant's co-pending PCT application no. PCT/CA2014/000849, filed Nov. 27, 2014 and entitled "Method, System and Apparatus for Quantitative Surgical Image Registration" which is incorporated herein by reference. Further, due to the use of the same scanning parameters to acquire the first and second images, registration may be simplified because voxel values can be compared directly (that is, without scaling) between images 400 and 500. The registration of images 400 and 500 can also include conventional matching techniques to account for tissue deformation (the tissue sample depicted in image 500 may be deformed in comparison to its shape within patient 104).

Figure 6:
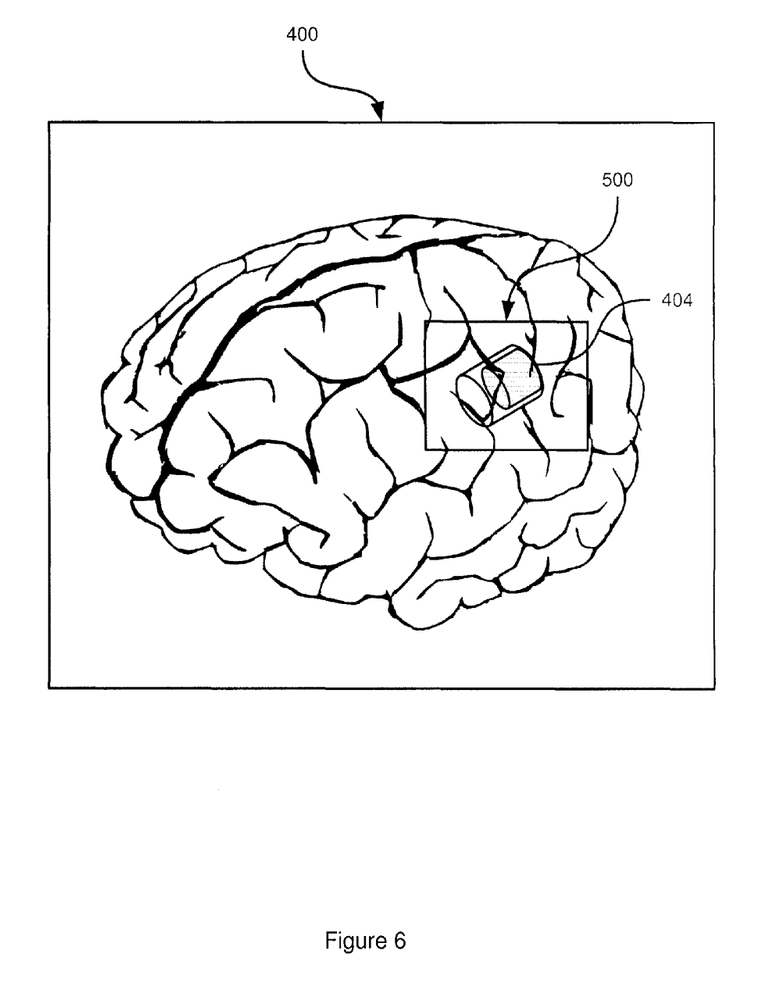
FIG. 6 depicts the images of FIGS. 4 and 5 registered with each other, according to a non-limiting embodiment.

An example of images 400 and 500 registered to one another is shown in FIG. 6. Having registered images 400 and 500, computing device 200 is configured to determine whether the target region (in the present example, the region depicting tumor 404) is entirely contained within second image 200. The determination can therefore include, for example, detecting the edges of tumor 404 in second image 500 and comparing the detected edges to the target region in image 400. As seen in FIG. 6, second image 500 does entirely encompass tumor 404, and thus the determination at block 330 is affirmative. In other words, when the entire target region is depicted in second image 500, the entire target portion of patient 104's brain (which corresponds to the target region) is contained within sample 504.

Following the determination at block 330, computing device 200 is configured to present, for example on display 110, an indication of whether the tissue sample contains the entire target portion, based on the comparison effected at block 330.

Figure 7:
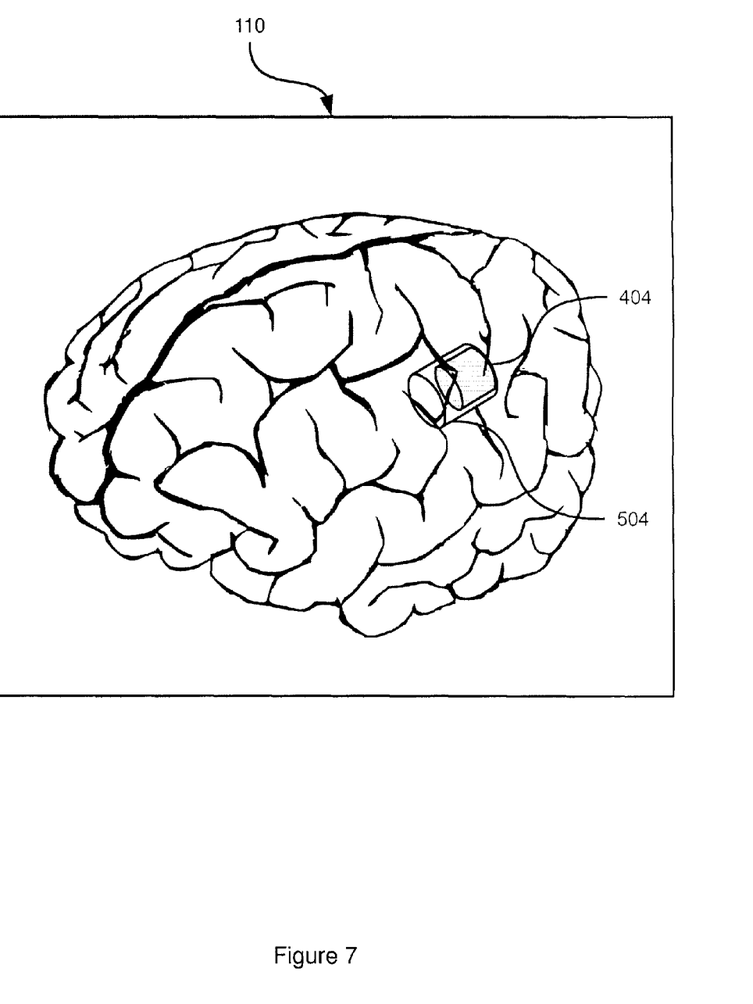
FIG. 7 depicts an example performance of block 335 of FIG. 3, according to a non-limiting embodiment.

When the determination at block 330 is affirmative, computing device 200 can be configured, at block 335, to present the above-mentioned indication on display 110 in the form of a confirmation that the target region is entirely contained within second image 500 (and therefore, that the target portion of the volume of tissue is entirely contained within sample 504). FIG. 7 depicts an example interface presented on display 110, in which the location of sample 504 is overlaid on image 400, depicting tumor 404 (as shown in image 400) as being contained entirely within sample 504.

When the determination at block 330 is negative, computing device 200 is configured to proceed to block 340 and present the above-mentioned indication on display 110 in the form of a warning that the target region is not entirely contained within second image 500 (and therefore, that the target portion of the volume of tissue is not entirely contained within sample 504).

Figure 8:
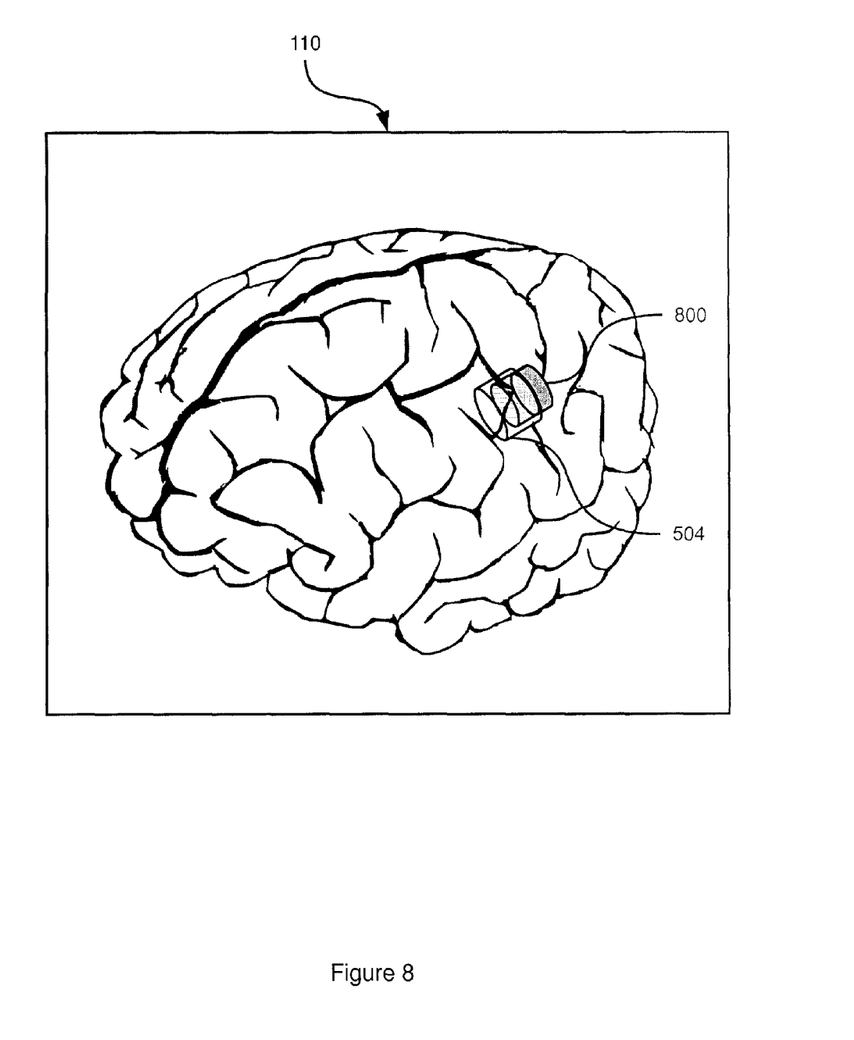
FIG. 8 depicts an example performance of block 340 of FIG. 3, according to a non-limiting embodiment.

Turning to FIG. 8, an example interface presented on display 110 as a result of the performance of block 340 is depicted. It is assumed that prior to the interface shown in FIG. 8 being presented, a sample of tissue was resected that did not contain the entirety of tumor 404. As seen in FIG. 8, computing device 200 produces an interface in which the boundaries of sample 504 are shown, and in which a portion 800 of tumor 404 falling outside of the second image is highlighted (by way of contrast, colour, and the like). The interface shown in FIG. 8 provides a warning that the sample resected from patient 104 does not contain the entire target region that was intended to be resected. In other embodiments, sample 504 and the successfully resected portion of tumor 404 can be omitted from the interface shown in FIG. 8, leaving only the highlighted portion 800 that remains to be resected.

Various imaging protocols can be employed to obtain the first and second images discussed above. For example, when the imaging modality employed is MRI, the scanning parameters can include those in any suitable T1-weighted imaging protocol, or those in a combination of diffusion-weighted imaging (DWI) and a T2-weighted imaging protocol.

Variations to the above methods and systems are contemplated. In some embodiments, for example, computing device 200 can be configured to perform an additional determination intraoperatively. During the surgical procedure, computing device 200 can receive and locations (e.g. from tracking system 112) for each surgical instrument in the field of view of tracking system 112, and store those locations in memory 204.

Processor 202 can be configured, either upon receipt of input data indicating that the resection of a tissue sample is complete, or at predetermined intervals during the procedure, to generate a volume of the patient tissue (e.g. the brain of patient 104) encompassed by the stored tracked locations. In other words, the tracked locations, considered as a set, represent a cloud of points within the patient tissue (tracked locations lying outside the patient tissue, for example outside patient 104's head, can be discarded or ignored). Having determined the volume of patient tissue contained within the above-mentioned cloud, processor 202 is configured to determine whether the target volume received at block 315 is entirely contained within the cloud. If the target volume is entirely contained within the cloud, processor 202 can proceed to block 335. In other words, the resection can be assumed to have been successful. Otherwise, processor 202 can proceed to block 340. In other words, if no tracked surgical instruments have had locations surrounding the entirety of the target volume, there is an increased likelihood that the entire target volume has not been resected.

The above-mentioned storage of tracked instrument locations and the above-mentioned determinations can be performed instead of blocks 320-330, or in addition to blocks 320-330. For example, in some embodiments processor 202 can be configured to perform both types of verification (instrument tracking and blocks 320-330) and perform the determination at block 330 based on the results of both types. When the two verifications conflict (e.g. part of the target volume is not encompassed by the cloud of locations, but the second image does contain the entire target volume), an intermediate state can be presented, instead of a warning or a confirmation. In other embodiments, one of the types of verification can override the other (e.g. in cases of conflict, the imaging-based verification of blocks 320-330 takes precedence).

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

We claim:

1. A method of automatically evaluating resection accuracy, comprising:
preoperatively obtaining a first image of a volume of patient tissue using an imaging modality configured according to a scanning parameter, wherein obtaining the first image comprises sending an instruction including the scanning parameter to a first imaging device, and wherein the first imaging device is a first MRI scanner; the scanning parameter defining a first imaging protocol implemented with the first imaging modality to acquire the first image;
storing the scanning parameter in a memory;
receiving and storing, in association with the first image, an identifier of a target region corresponding to a target portion of the volume;
responsive to resection of a tissue sample from the volume, obtaining a second image of the tissue sample using the imaging modality configured according to the scanning parameter for implementing the first imaging protocol to acquire the second image, wherein obtaining the second image comprises sending an instruction including the scanning parameter to a second imaging device, and wherein the second imaging device is a second MRI scanner;
determining, based on a comparison of the first image and the second image, whether the entire target region is represented in the second image; and
controlling an output device to present an indication, based on the determination, of whether the tissue sample contains the entire target portion.

2. The method of claim 1, wherein the determining includes registering the second image to the first image.

3. The method of claim 1, wherein the second image is obtained intraoperatively.

4. The method of claim 1, wherein the second image is obtained postoperatively.

5. The method of claim 1, wherein the target portion is a tumor.

6. The method of claim 1, further comprising:
receiving, from a tracking system, a plurality of locations of a surgical instrument within the volume of patient tissue;
computing a tracked portion of the volume encompassed by the locations;
assessing whether the target portion is contained within the tracked portion; and
controlling the output device to present the indication based on the determining and the assessing.

7. A computing device for automatically evaluating resection accuracy; comprising:
a memory;

an output device; and a processor interconnected with the memory and the output device, the processor configured to:

preoperatively obtain a first image of a volume of patient tissue using an imaging modality configured according to a scanning parameter, by sending an instruction including the scanning parameter to a first imaging device, wherein the first imaging device is a first MRI scanner; the scanning parameter defining a first imaging protocol implemented with the first imaging modality to acquire the first image;

store the scanning parameter in the memory;

receive and store, in association with the first image, an identifier of a target region corresponding to a target portion of the volume;

responsive to resection of a tissue sample from the volume, obtain a second image of the tissue sample using the imaging modality configured according to the scanning parameter for implementing the first imaging protocol to acquire the second image, by sending an instruction including the scanning parameter to a second imaging device, wherein the second imaging device is a second MRI scanner;

determine, based on a comparison of the first image and the second image, whether the entire target region is represented in the second image; and control the output device to present an indication, based on the determination, of whether the tissue sample contains the entire target portion.

8. The computing device of claim 7, the processor further configured to determine whether the entire target region is represented in the second image by registering the second image to the first image.

9. The computing device of claim 7, the processor further configured to obtain the second image intraoperatively.

10. The computing device of claim 7, the processor further configured to obtain the second image postoperatively.

11. The computing device of claim 7, wherein the target portion is a tumor.

12. The computing device of claim 7, the processor further configured to:

receive, from a tracking system, a plurality of locations of a surgical instrument within the volume of patient tissue;

compute a tracked portion of the volume encompassed by the locations;

assess whether the target portion is contained within the tracked portion; and control the output device to present the indication based on the determining and the assessing.

13. The computing device of claim 7, wherein the output device includes a display.

* * * * *